(12) United States Patent
Kohring et al.

(10) Patent No.: US 11,395,887 B2
(45) Date of Patent: Jul. 26, 2022

(54) INTRANASAL DEVICE WITH INLET INTERFACE

(71) Applicant: Impel Pharmaceuticals Inc., Seattle, WA (US)

(72) Inventors: Craig Frederick Kohring, Seattle, WA (US); Christopher William Fuller, Seattle, WA (US)

(73) Assignee: Impel Pharmaceuticals Inc., Seattle, WA (US)

(*) Notice: Subject to any disclaimer, the term of this patent is extended or adjusted under 35 U.S.C. 154(b) by 743 days.

(21) Appl. No.: 16/198,312

(22) Filed: Nov. 21, 2018

(65) Prior Publication Data
US 2019/0151576 A1    May 23, 2019

Related U.S. Application Data

(60) Provisional application No. 62/589,326, filed on Nov. 21, 2017.

(51) Int. Cl.
*A61M 15/00* (2006.01)
*A61M 15/08* (2006.01)

(52) U.S. Cl.
CPC ...... *A61M 15/003* (2014.02); *A61M 15/0035* (2014.02); *A61M 15/08* (2013.01);
(Continued)

(58) Field of Classification Search
CPC ............ A61M 15/003; A61M 15/0028; A61M 15/033; A61M 15/0035; A61M 15/08;
(Continued)

(56) References Cited

U.S. PATENT DOCUMENTS 2,587,215 A   2/1952  Priestly
2,933,259 A   4/1960  Raskin
(Continued)

FOREIGN PATENT DOCUMENTS

CA       2415845 A1    4/2002
CN    103635218 A      3/2014
(Continued)

OTHER PUBLICATIONS

Appasaheb, et al., "Review on Intranasal Drug Delivery System", Journal of Advanced Pharmacy Education and Research, vol. 3, Issue 4, Oct. 2013, 14 pages.
(Continued)

*Primary Examiner* — Timothy A Stanis
*Assistant Examiner* — Matthew R Moon
(74) *Attorney, Agent, or Firm* — Fenwick & West LLP

(57) ABSTRACT

A device for delivering a compound to the olfactory region of the nasal cavity includes an actuator body and a tip that removably couples to the actuator body. The actuator body includes a propellant channel in fluid communication with a propellant canister. The tip includes an exit channel, an inlet interface, one or more grooves, and an outlet orifice. The exit channel extends between a proximal end and a distal end of the tip. The inlet interface is positioned about a distal end of the exit channel, and the inlet interface couples to a compound container containing the compound. The grooves are positioned about the inlet interface and direct propellant from the propellant channel into the compound container, thereby agitating and entraining the compound in the compound container with the released propellant. The compound and the propellant then travel through the exit channel and out the outlet orifice.

13 Claims, 19 Drawing Sheets

(52) U.S. Cl.
CPC ....... *A61M 15/009* (2013.01); *A61M 2202/04* (2013.01); *A61M 2202/064* (2013.01); *A61M 2205/8225* (2013.01); *A61M 2206/20* (2013.01)

(58) Field of Classification Search
CPC ............ A61M 15/009; A61M 2202/04; A61M 2202/064; A61M 2205/8225; A61M 2206/20; A61M 11/02; A61M 15/0036
See application file for complete search history.

(56) References Cited

U.S. PATENT DOCUMENTS

| | | | |
|---|---|---|---|
| 3,425,414 A | | 2/1969 | Roche |
| 3,653,380 A | | 4/1972 | Hansen |
| 3,888,253 A | | 6/1975 | Watt et al. |
| 3,906,950 A | | 9/1975 | Cocozza |
| 3,908,654 A | | 9/1975 | Lhoest et al. |
| 3,971,377 A | | 7/1976 | Damani |
| 4,095,596 A | | 6/1978 | Grayson |
| 4,187,985 A | | 2/1980 | Goth |
| 4,227,522 A | | 10/1980 | Carris |
| 4,353,365 A | | 10/1982 | Hallworth et al. |
| 4,412,573 A | | 11/1983 | Zdeb |
| 4,620,670 A | | 11/1986 | Hughes |
| 4,702,415 A | | 10/1987 | Hughes |
| 4,896,832 A | | 1/1990 | Howlett |
| 4,995,385 A | | 2/1991 | Valentini et al. |
| 5,074,318 A | * | 12/1991 | Campbell ............ A01K 11/006 128/899 |
| 5,224,471 A | | 7/1993 | Marelli et al. |
| 5,307,953 A | | 5/1994 | Regan |
| 5,331,954 A | | 7/1994 | Rex et al. |
| 5,349,947 A | | 9/1994 | Newhouse et al. |
| 5,382,236 A | | 1/1995 | Otto et al. |
| 5,398,850 A | | 3/1995 | Sancoff et al. |
| 5,435,282 A | | 7/1995 | Haber et al. |
| 5,505,193 A | | 4/1996 | Ballini et al. |
| 5,516,006 A | | 5/1996 | Meshberg |
| 5,619,985 A | * | 4/1997 | Ohki ................. A61M 15/0028 128/203.15 |
| 5,711,488 A | | 1/1998 | Lund |
| 5,715,811 A | | 2/1998 | Ohki et al. |
| 5,797,390 A | | 8/1998 | McSoley |
| 5,814,020 A | | 9/1998 | Gross |
| 5,819,730 A | | 10/1998 | Stone et al. |
| 5,823,183 A | | 10/1998 | Casper et al. |
| 5,881,719 A | | 3/1999 | Gottenauer et al. |
| 5,901,703 A | | 5/1999 | Ohki et al. |
| 5,906,198 A | | 5/1999 | Flickinger |
| 5,910,301 A | | 6/1999 | Farr et al. |
| 5,954,696 A | | 9/1999 | Ryan |
| 6,055,979 A | | 5/2000 | Fuchs |
| 6,062,213 A | | 5/2000 | Fuisz et al. |
| 6,079,634 A | | 6/2000 | Noakes et al. |
| 6,092,522 A | | 7/2000 | Calvert et al. |
| 6,145,703 A | | 11/2000 | Opperman |
| 6,158,676 A | | 12/2000 | Hughes |
| 6,180,603 B1 | | 1/2001 | Frey |
| 6,186,141 B1 | | 2/2001 | Pike et al. |
| 6,189,739 B1 | | 2/2001 | von Schuckmann |
| 6,294,153 B1 | | 9/2001 | Modi |
| 6,302,101 B1 | | 10/2001 | Py |
| 6,313,093 B1 | | 11/2001 | Frey |
| 6,347,789 B1 | | 2/2002 | Rock |
| 6,367,471 B1 | | 4/2002 | Genosar et al. |
| 6,367,473 B1 | | 4/2002 | Käfer |
| 6,382,465 B1 | | 5/2002 | Greiner Perth |
| 6,410,046 B1 | | 6/2002 | Lerner |
| 6,491,940 B1 | | 12/2002 | Levin |
| 6,540,983 B1 | | 4/2003 | Adjei et al. |
| 6,569,463 B2 | | 5/2003 | Patel et al. |
| 6,585,172 B2 | | 7/2003 | Arghyris |
| 6,585,957 B1 | | 7/2003 | Adjei et al. |
| 6,585,958 B1 | | 7/2003 | Keller et al. |
| 6,595,202 B2 | | 7/2003 | Gañán Calvo |
| 6,622,721 B2 | | 9/2003 | Vedrine et al. |
| 6,644,305 B2 | | 11/2003 | MacRae et al. |
| 6,644,309 B2 | | 11/2003 | Casper et al. |
| 6,647,980 B1 | | 11/2003 | Gizurarson |
| 6,681,767 B1 | | 1/2004 | Patton et al. |
| 6,684,879 B1 | | 2/2004 | Coffee et al. |
| 6,701,916 B2 | | 3/2004 | Mezzoli |
| 6,715,485 B1 | | 4/2004 | Djupesland |
| 6,734,162 B2 | | 5/2004 | Van Antwerp et al. |
| 6,810,872 B1 | | 11/2004 | Ohki et al. |
| 6,923,988 B2 | | 8/2005 | Patel et al. |
| 7,033,598 B2 | | 4/2006 | Lerner |
| 7,051,734 B2 | | 5/2006 | Casper et al. |
| 7,163,013 B2 | | 1/2007 | Harrison |
| 7,182,277 B2 | | 2/2007 | Vedrine et al. |
| 7,200,432 B2 | | 4/2007 | Lerner et al. |
| 7,214,209 B2 | | 5/2007 | Mazzoni |
| 7,231,919 B2 | | 6/2007 | Giroux |
| 7,258,119 B2 | | 8/2007 | Mazzoni |
| 7,296,566 B2 | | 11/2007 | Alchas |
| 7,347,201 B2 | | 3/2008 | Djupesland |
| 7,377,901 B2 | | 5/2008 | Djupesland et al. |
| 7,476,689 B2 | | 1/2009 | Santus et al. |
| 7,481,218 B2 | | 1/2009 | Djupesland |
| 7,543,581 B2 | | 6/2009 | Djupesland |
| 7,655,619 B2 | | 2/2010 | During et al. |
| 7,740,014 B2 | | 6/2010 | Djupesland |
| 7,784,460 B2 | | 8/2010 | Djupesland et al. |
| 7,799,337 B2 | | 9/2010 | Levin |
| 7,832,394 B2 | | 11/2010 | Schechter et al. |
| 7,841,337 B2 | | 11/2010 | Djupesland |
| 7,841,338 B2 | | 11/2010 | Dunne et al. |
| 7,854,227 B2 | | 12/2010 | Djupesland |
| 7,866,316 B2 | | 1/2011 | Giroux |
| 7,905,229 B2 | | 3/2011 | Giroux et al. |
| 7,934,503 B2 | | 5/2011 | Djupesland et al. |
| 7,975,690 B2 | | 7/2011 | Djupesland |
| 7,994,197 B2 | | 8/2011 | Cook et al. |
| 8,001,963 B2 | | 8/2011 | Giroux |
| 8,047,202 B2 | | 11/2011 | Djupesland |
| 8,119,639 B2 | | 2/2012 | Cook et al. |
| 8,122,881 B2 | | 2/2012 | Giroux |
| 8,146,589 B2 | | 4/2012 | Djupesland |
| 8,171,929 B2 | | 5/2012 | Djupesland et al. |
| 8,327,844 B2 | | 12/2012 | Djupesland |
| 8,408,427 B2 | | 4/2013 | Wong |
| 8,448,637 B2 | | 5/2013 | Giroux |
| 8,496,002 B2 | | 7/2013 | Ellwanger |
| 8,511,303 B2 | | 8/2013 | Djupesland |
| 8,517,026 B2 | | 8/2013 | Amon |
| 8,522,778 B2 | | 9/2013 | Djupesland |
| 8,550,073 B2 | | 10/2013 | Djupesland |
| 8,555,877 B2 | | 10/2013 | Djupesland |
| 8,555,878 B2 | | 10/2013 | Djupesland |
| 8,596,278 B2 | | 12/2013 | Djupesland |
| 8,733,342 B2 | | 5/2014 | Giroux et al. |
| 8,757,146 B2 | | 6/2014 | Hoekman et al. |
| 8,763,605 B2 | * | 7/2014 | Jones ................. A61M 15/002 128/203.15 |
| 8,800,555 B2 | | 8/2014 | Djupesland |
| 8,839,790 B2 | | 9/2014 | Beck Arnon |
| 8,875,794 B2 | | 11/2014 | Carlsen et al. |
| 8,899,229 B2 | | 12/2014 | Djupesland et al. |
| 8,899,230 B2 | | 12/2014 | Immel |
| 8,910,629 B2 | | 12/2014 | Djupesland et al. |
| 8,925,544 B2 | | 1/2015 | Flickinger |
| 8,978,647 B2 | | 3/2015 | Djupesland et al. |
| 8,987,199 B2 | | 3/2015 | Abdel Maksoud et al. |
| 9,010,325 B2 | | 4/2015 | Djupesland et al. |
| 9,038,630 B2 | | 5/2015 | Djupesland et al. |
| 9,067,034 B2 | | 6/2015 | Djupesland et al. |
| 9,072,857 B2 | | 7/2015 | Djupesland |
| 9,101,539 B2 | | 8/2015 | Nagata et al. |
| 9,119,932 B2 | | 9/2015 | Djupesland |
| 9,180,264 B2 | | 11/2015 | Young et al. |
| 9,272,104 B2 | | 3/2016 | Djupesland |
| 9,446,207 B2 | | 9/2016 | Jung |
| 2002/0017294 A1 | | 2/2002 | Py |

(56) References Cited

U.S. PATENT DOCUMENTS

| | | |
|---|---|---|
| 2002/0054856 A1 | 5/2002 | Jones |
| 2002/0092520 A1 | 7/2002 | Casper et al. |
| 2003/0015191 A1 | 1/2003 | Armstrong et al. |
| 2003/0017119 A1 | 1/2003 | Rabinowitz et al. |
| 2003/0158527 A1 | 8/2003 | Mezzoli |
| 2003/0217748 A1 | 11/2003 | Giroux |
| 2004/0068222 A1 | 4/2004 | Brian |
| 2004/0153033 A1 | 8/2004 | Mazzoni |
| 2004/0238574 A1 | 12/2004 | Merk et al. |
| 2005/0023376 A1 | 2/2005 | Anderson |
| 2005/0028812 A1 | 2/2005 | Djupesland |
| 2005/0036985 A1 | 2/2005 | Ensoli |
| 2005/0098172 A1 | 5/2005 | Anderson |
| 2005/0142072 A1 | 6/2005 | Birch et al. |
| 2005/0274378 A1 | 12/2005 | Bonney et al. |
| 2006/0107957 A1 | 5/2006 | Djupesland |
| 2006/0219813 A1 | 10/2006 | Morrison |
| 2006/0240092 A1 | 10/2006 | Breitenkamp et al. |
| 2007/0056585 A1 | 3/2007 | Davies et al. |
| 2007/0068514 A1 | 3/2007 | Giroux |
| 2007/0074722 A1 | 4/2007 | Giroux et al. |
| 2007/0119451 A1 | 5/2007 | Wang et al. |
| 2007/0131224 A1 | 6/2007 | Giroux |
| 2007/0172517 A1 | 7/2007 | Ben Sasson et al. |
| 2007/0202051 A1 | 8/2007 | Schuschnig |
| 2008/0054099 A1 | 3/2008 | Giroux et al. |
| 2008/0163874 A1 | 7/2008 | Djupesland |
| 2008/0178871 A1 | 7/2008 | Genova et al. |
| 2008/0305077 A1 | 12/2008 | Frey et al. |
| 2009/0320832 A1 | 12/2009 | Djupestand |
| 2011/0053859 A1 | 3/2011 | Deadwyler et al. |
| 2011/0057055 A1 | 3/2011 | Wong |
| 2012/0195959 A1 | 8/2012 | Ishii |
| 2013/0213397 A1* | 8/2013 | Curtis ............... A61M 15/0033 128/203.15 |
| 2014/0014104 A1 | 1/2014 | Hoekman et al. |
| 2014/0060535 A1 | 3/2014 | Tsutsui |
| 2014/0083424 A1 | 3/2014 | Haekman et al. |
| 2014/0170220 A1 | 6/2014 | Cartt et al. |
| 2014/0343494 A1 | 11/2014 | Hoekman et al. |
| 2015/0057287 A1 | 2/2015 | Cook et al. |
| 2015/0122257 A1 | 5/2015 | Winkler et al. |
| 2015/0136131 A1* | 5/2015 | Holakovsky ......... B65D 47/283 128/203.15 |
| 2015/0216823 A1 | 8/2015 | Chatterjee |
| 2015/0258178 A1 | 9/2015 | Gong |
| 2016/0058960 A1 | 3/2016 | Papania et al. |
| 2016/0101245 A1 | 4/2016 | Hoekman et al. |
| 2016/0228433 A1 | 8/2016 | Haruta et al. |
| 2017/0128364 A1 | 5/2017 | Kamishita et al. |

FOREIGN PATENT DOCUMENTS

| | | |
|---|---|---|
| DE | 19518580 A1 | 11/1996 |
| DE | 102013100473 A1 | 7/2014 |
| EP | 1165044 A2 | 1/2002 |
| GB | 806284 A | 12/1958 |
| GB | 1517642 A | 7/1978 |
| JP | H08243163 A | 9/1996 |
| JP | H08322934 A | 12/1996 |
| JP | 3547605 B2 | 7/2004 |
| JP | 2013094400 A | 5/2013 |
| WO | WO 1986001731 A1 | 3/1986 |
| WO | WO 1999013930 A1 | 3/1999 |
| WO | WO 2000054887 A1 | 9/2000 |
| WO | WO 2001036033 A2 | 5/2001 |
| WO | WO 2002009707 A1 | 2/2002 |
| WO | WO 2007012853 A1 | 2/2007 |
| WO | WO 2008059385 A2 | 5/2008 |
| WO | WO 2009/100383 A2 | 8/2009 |
| WO | WO 2012/119153 A2 | 9/2012 |
| WO | WO 2014/179228 A1 | 11/2014 |
| WO | WO-2017/044897 A1 | 3/2017 |

OTHER PUBLICATIONS

Baron, "Orally Inhaled Dihydroergotamine; Reviving and Improving a Classic", Future Neurology, May 2011, 11 pages.

Constantino, et al., "Intranasal administration of acetylcholinesterase inhibitors", BMC Neuroscience, Dec. 10, 2008, 3 pages.

EP Office Action for 14727320.5, dated Nov. 9, 2016, 6 pages.

EP Search Report for 09707800.0 dated Jul. 1, 2015, 12 pages.

EP Search Report for 11818832.5 dated Sep. 24, 2014, 6 pages.

Hanson, et al., "Intranasal delivery of growth differentiation factor 5 to the central nervous system", Drug Delivery, 19(3):149-54, Feb. 2012, 7 pages.

Hoekman, J.D., "The Impact of Enhanced Olfactory Deposition and Retention on Direct Nose-to-Brain Drug Delivery", UMI Dissertation Publishing, Apr. 11, 2011, 181 pages.

International Search Report for PCT/US/2009/033468 dated Dec. 2, 2009, 5 pages.

Kumar, et al., "Nasal Drug Delivery: A Potential Route for Brain Targeting" The Pharma Innovation Journal, vol. 2, No. 1, Mar. 2013. 9 pages.

Ozsoy, et al., "Nasal Delivery of High Molecular Weight Drugs", Molecules Journal, Sep. 23, 2009, 26 pages.

Parvathi, "Intranasal Drug Delivery to Brain: An Overview," published in the International Journal of Research in Pharmacy and Chemistry 2012, 2(3), 7 pages.

PCT International Search Report and Written Opinion, PCT Application No. PCT/US2018/62296, dated Mar. 11, 2019, 15 pages.

PCT International Search Report and Written Opinion, PCT Application No. PCT/US2018/62280, dated Feb. 11, 2019, 43 pages.

Renner, et al., "Intranasal delivery of growth differentiation factor 5 to the central nervous system," Drug Delivery, Feb. 2012, 7 pages.

Stevens, et al., "Systemic and Direct Nose-to-Brain Transport Pharmacokinetic Model for Remoxipride after Intravenous and Intranasal Administration", in "Drug Metabolism and Disposition", The American Society for Pharmacology and Experimental Therapeutics, 2011, vol. 39, No. 12, 8 pages.

Talegaonkar, et al., "Intranasal delivery: an approach to bypass the blook brain barrier", Indian J Pharmacol, Jun. 2004, vol. 36, Issue 3, 8 pages.

The PCT Search Report and Written Opinion dated Mar. 27, 2012 for PCT application No. PCT/US2011/048435, 14 pages.

Westin et al., "Direct Nose to Brain Transfer of Morphine After Nasal Administration to Rats", Pharmaceutical Research, vol. 23, No. 3, Mar. 2006, 8 pgs.

Westin, "Olfactory Transfer of Analgesic Drugs After Nasal Administration", Digital Comprehensive Summaries of Uppsala Dissertations from the Faculty of Pharmacy 55, May 11, 2007, 66 pages.

Yamada, et al., "Nose-to-brain delivery of TS-002, prostaglandin D2 analogue", Journal of Drug Targeting, Jan. 2007, 9 pages.

Yimam, et al., "Effects of lipid association on lomustine (CCNU) administered intracerebrally to syngeneic 36B-10 rat brain tumors", Cancer Letters 244(2), Dec. 2006, 9 pages.

Ying, "The nose may help the brain: intranasal drug delivery for treating neurological diseases" Future Medicine, 3(1), Jan. 2008, 4 pages.

Zhang, et al., "The brain targeting efficiency following nasally applied MPEG-PLA nanoparticles in rats", Journal of Drug Targeting, Jun. 2006, 11 pages.

European Patent Office, Extended European Search Report, European Patent Application No. 18880741.6, dated Jul. 15, 2021, eight pages.

Chinese Patent Office, Office Action, Chinese Patent Application No. 201880075221.1, dated Oct. 22, 2021, 10 pages, (with concise explanation of relevance).

* cited by examiner

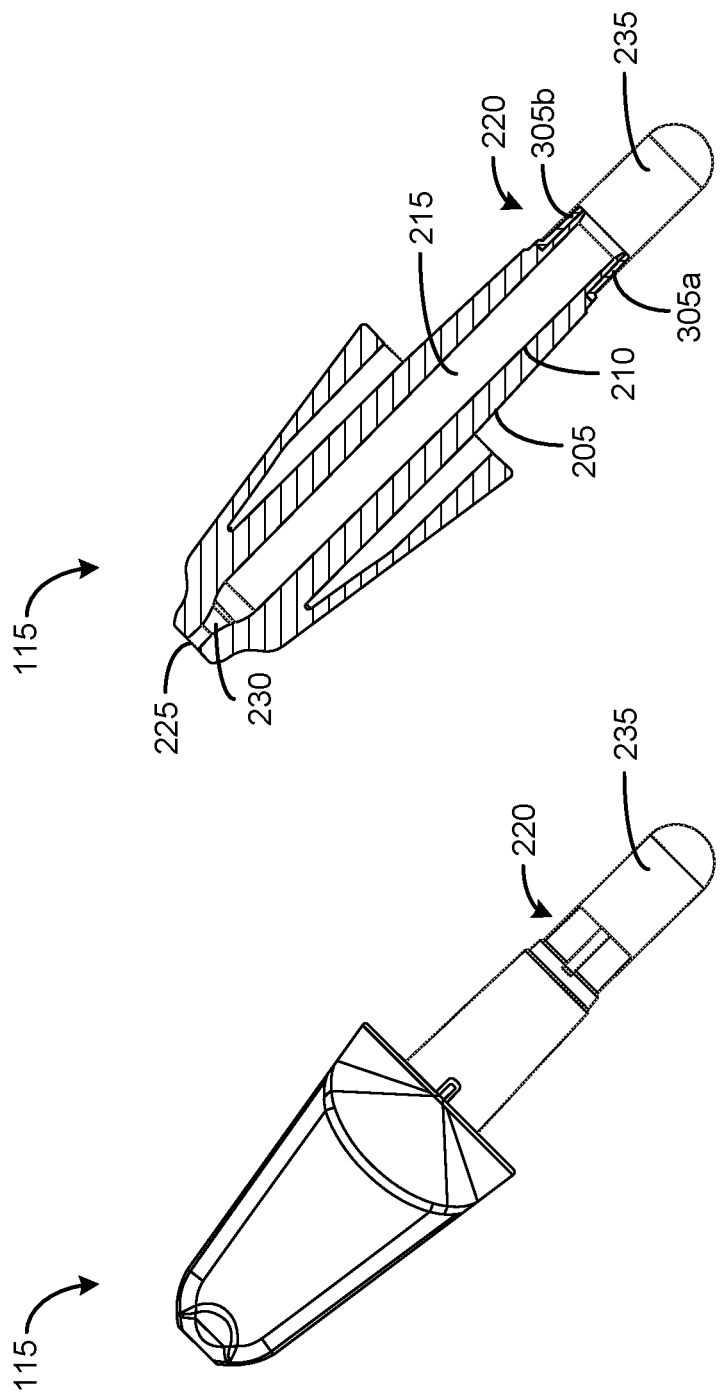

INTRANASAL DEVICE WITH INLET INTERFACE

CROSS-REFERENCE TO RELATED APPLICATION

This application claims the benefit of U.S. Provisional Application No. 62/589,326, filed on Nov. 21, 2017, which is herein incorporated by reference in its entirety.

BACKGROUND

Depositing drug in the upper nasal cavity is difficult to accomplish due to the complex architecture of the nasal cavity and the turbinate guided air path for inhaled breath through the nose. These natural structures act to prevent materials from depositing in the upper nasal cavity as a way to protect this entry way into the central nervous system (CNS). Existing nasal drop or spray devices are designed to saturate the lower nasal cavity. Drug deposited on the lower nasal cavity is absorbed into the blood stream instead of the CNS, eliminating an advantage of using the nasal route for CNS delivery.

A more elegant approach to the intranasal delivery of compounds or mixtures is needed.

SUMMARY

A device for delivering a compound to the upper nasal cavity is described. In one embodiment, the device includes an actuator body and a tip configured to removably couple to the actuator body. The actuator body comprises a propellant channel that is configured to be in fluid communication with a canister containing a propellant. The tip comprises an outer wall and an inner wall, an exit channel, an inlet interface, one or more grooves, and an outlet orifice. The inner wall forms the exit channel which extends between a proximal end and a distal end of the tip. The inlet interface is positioned about a distal end of the outer wall, and the inlet interface is configured to couple to a compound container containing the compound. The one or more grooves are positioned about the inlet interface, where, when the compound container is coupled to the inlet interface, each groove is in fluid communication with the propellant channel and the exit channel. The outlet orifice is disposed at the distal end of the exit channel, such that propellant released from the canister travels through the propellant channel and the one or more grooves, into the compound container, thereby contacting the compound and propelling the compound through the exit channel and out the outlet orifice.

In one embodiment, the one or more grooves are oriented on the inlet interface such that the one or more grooves are configured to direct propellant released from the canister into the compound container in an orthogonal or near-orthogonal direction relative to a bottom surface of the compound container, thereby agitating and entraining the compound in the compound container with the released propellant.

This configuration enables a user to load and unload a compound container onto the tip for administration of the compound.

The invention will best be understood by reference to the following detailed description of various embodiments, taken in conjunction with any accompanying drawings. The discussion below is descriptive, illustrative and exemplary and is not to be taken as limiting the scope defined by any appended claims.

BRIEF DESCRIPTION OF THE DRAWINGS

FIG. 6 is a perspective view of the tip with the capsule attached, in accordance with one or more embodiments FIG. 7 is a cross-sectional view of the tip with the capsule attached, in accordance with one or more embodiments.

The figures depict embodiments of the present disclosure for purposes of illustration only. One skilled in the art will readily recognize from the following description that alternative embodiments of the structures and methods illustrated herein may be employed without departing from the principles, or benefits touted, of the disclosure described herein.

DETAILED DESCRIPTION

Unless stated otherwise, the following terms and phrases as used herein are intended to have the following meanings:

When trade names are used herein, applicants intend to independently include the trade name product formulation, the generic drug, and the active pharmaceutical ingredient(s) of the trade name product.

For clarity of disclosure, and not by way of limitation, the detailed description of the invention is divided into the subsections which follow.

Unless defined otherwise, all technical and scientific terms used herein have the same meaning as commonly understood by one of ordinary skill in the art pertinent to the methods and compositions described. The following references provide one of skill with a non-exclusive guide to a general definition of many of the terms used herein: Hale & Margham, The Harper Collins Dictionary of Biology (Harper Perennial, New York, N.Y., 1991); King & Stansfield, A Dictionary of Genetics (Oxford University Press, 4th ed. 1990); Hawley's Condensed Chemical Dictionary (John Wiley & Sons, 13th ed. 1997); and Stedmans' Medical Dictionary (Lippincott Williams & Wilkins, 27th ed. 2000). As used herein, the following terms and phrases have the meanings ascribed to them unless specified otherwise.

Figure 1:
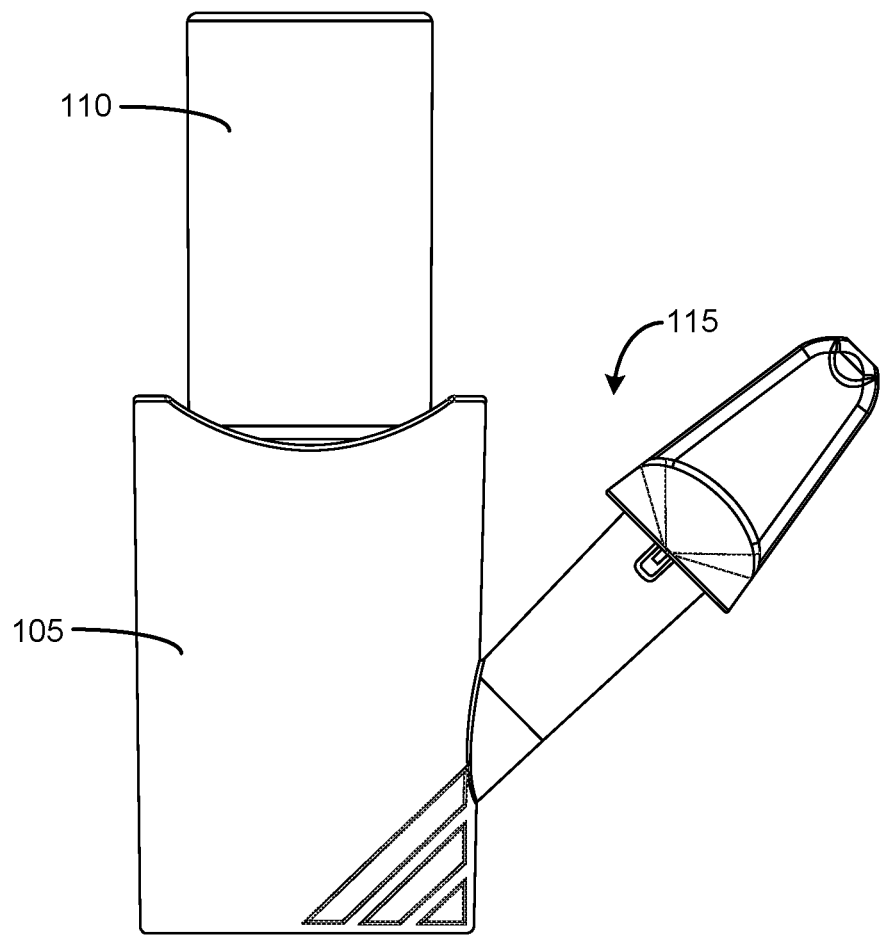
FIG. 1 is an intranasal drug delivery device, in accordance with one or more embodiments.
Figure 2:
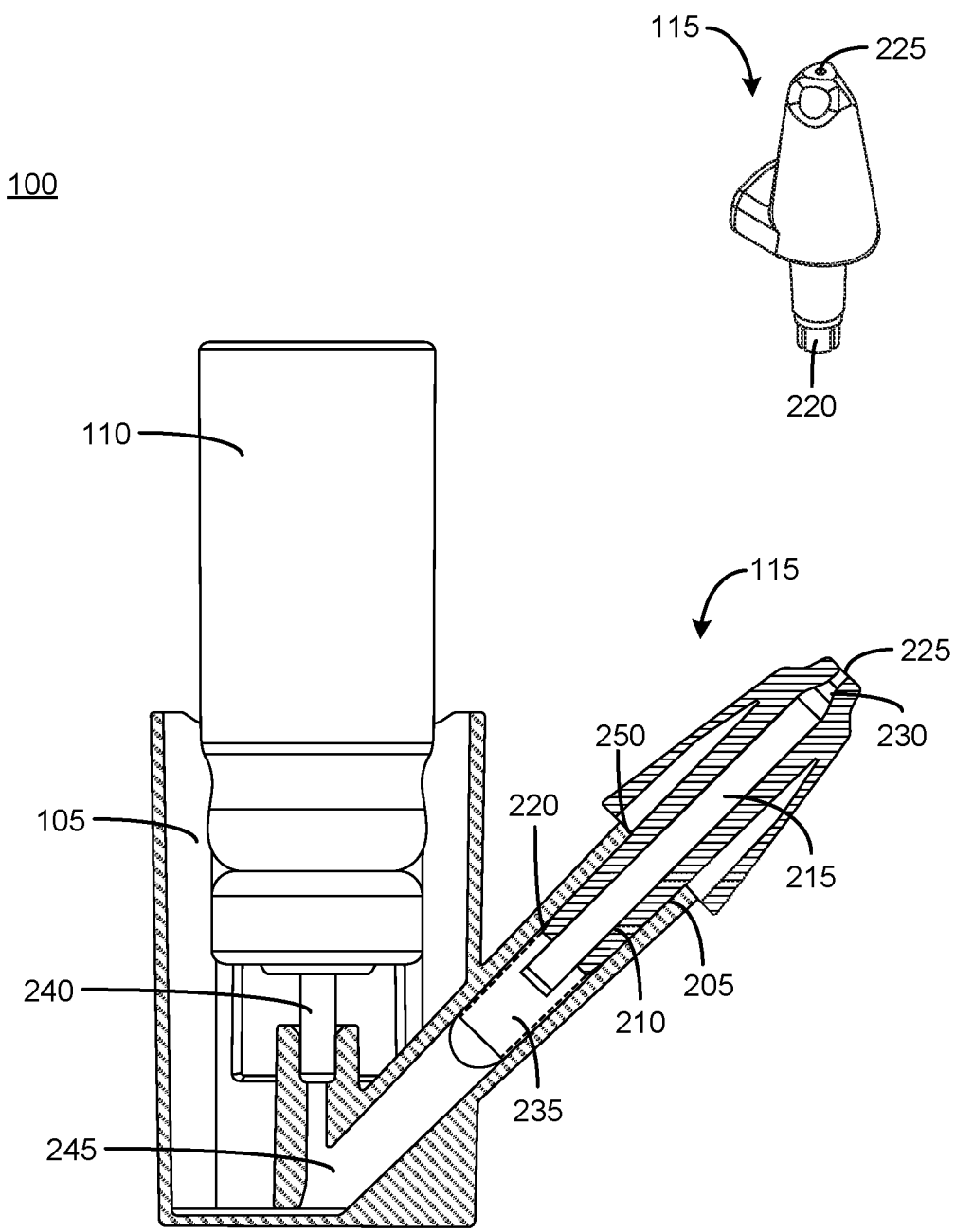
FIG. 2 illustrates a partial cross-sectional view of the device, in accordance with one or more embodiments.

As shown in FIGS. 1 and 2, the intranasal device 100 is designed to deliver a consistent mass of compound into the nasal cavity. For example, but not limited to, the compound may be an intranasal formulation in a powder form. The device 100 targets a specific region of the nasal cavity utilizing a narrow, targeted delivery plume. Specifically, the device 100 provides the compound to the upper one third of the nasal cavity. In one embodiment, the device 100 is used to administer the compound into the upper nasal cavity of a human. The upper nasal cavity includes the olfactory region and the middle and upper turbinate regions. In another embodiment, the device 100 is used to administer the compound into the upper nasal cavity of a non-human primate. The device 100 is also designed to simplify clinician loading of the compound into the device 100 and use thereof. The device 100 may be re-used to administer several doses of the compound.

FIG. 2 illustrates a partial cross-sectional view of the device 100 for delivering a compound intranasally. In the embodiment of FIG. 2, the device 100 includes an actuator body 105, a propellant canister 110, and a tip 115. The tip 115 includes an outer wall 205 and an inner wall 210, an exit channel 215, an inlet interface 220, one or more grooves 305 (shown in FIG. 3), an outlet orifice 225, and a nozzle 230. FIG. 2 illustrates the compound container 235 coupled to the inlet interface 220. The compound contained in the compound container 235 may be a liquid or a powder. In the embodiment of FIG. 2, the compound is a powder.

As shown in FIG. 2, the device 100 includes a propellant canister 110 positioned within the actuator body 105. The propellant canister 110 contains propellant. In one embodiment, the propellant may be pressurized. The propellant is a fluid, for example, a liquid or gas. In one aspect, the propellant is a liquid. In another aspect, the propellant is a gas. Propellants include pharmaceutically suitable propellants. Some examples of pharmaceutically suitable propellants include hydrofluoroalkane (HFA) including but not limited to HFA, HFA 227, HFA 134a, HFA-FP, HFA-BP and the like HFA's. In one aspect, the propellant is liquid HFA. In another aspect, the propellant is gaseous HFA. Additional examples of suitable propellants include nitrogen or chlorofluorocarbons (CFC). Additionally, propellants may be pressurized air (e.g. ambient air). The canister 110 may be a metered dose inhaler (MDI) device that includes a pressurized canister and metering valve 240 (including stem) to meter the propellant upon actuation. In one embodiment, a pump fitment (not shown) secures the metered valve 240 to the canister 110 and holds both components in place during device 100 use. One series of embodiments of the pump fitment consists of securing interfaces that retain the pump fitment within the actuator body 105, provide vertical displacement, and prevent rotation during installation of the canister 110.

The propellant canister 110 may have a capacity for distributing propellant for a certain number of doses. In one embodiment, the device 100 may be shipped without a canister 110 and the canister 110 may be loaded into the actuator body 105 by the user. In some embodiments, the propellant canister may be replaced with a new propellant canister, such that the device 100 may be reused. In one aspect, when the MDI device is actuated, a discrete amount of pressurized HFA fluid is released. The MDI may contain between about 30 to about 300 actuations, inclusive of endpoints, of HFA propellant. The amount of fluid propellant released upon actuation may be between about 20 μl and about 200 μl inclusive of endpoints, of liquid propellant.

The actuator body 105 comprises a propellant channel 245 that is in fluid communication with the propellant canister 110. The propellant channel 245 is in fluid communication with the inlet interface 220, which is configured to couple to the compound container 235 such that propellant released from the propellant canister 110 can be introduced into the compound container 235 via the one or more grooves 305 on the inlet interface 220. In the embodiment of FIG. 2, the propellant channel 245 includes a port 250 at a distal end for receiving the tip 115. In this configuration, the tip 115 may be coupled and decoupled to the actuator body 105 by inserting the tip 115 into the port 250. In other embodiments, the port 250 may be inserted into the tip 115. In some embodiments, the port 250 and/or the tip 115 may include a sealing interface that creates an airtight seal between the propellant channel 245 and the tip 115 such that propellant released from the canister 110 does not escape out of the propellant channel 245 and is directed to the inlet interface 220.

The tip 115 may be coupled and decoupled to the actuator body 105, which enables a user to load and unload a compound container 235 to and from the inlet interface 220. The tip 115 includes the outer wall 205 and the inner wall 210, where the inner wall forms the exit channel 215 which extends between a proximal end and a distal end of the tip 115. The inlet interface 220 is positioned about a distal end of the outer wall 205, and the inlet interface 220 couples the compound container 235. In the embodiment of FIG. 2, the inlet interface 220 is a collar that may be inserted into the compound container 235. In other embodiments, the inlet interface 220 may be a ring, band, port, or strap that interfaces with the compound container 235. The inlet interface 220 includes one or more grooves 305 (shown in FIG. 3) for directing propellant released from the canister 110 into the compound container 235 coupled to the inlet interface 220. The released propellant then contacts the compound within the compound container 235, agitating and entraining the compound and propelling the compound through the exit channel 215 and out the outlet orifice 225 located at a distal end of the exit channel 215. In the embodiment of FIG. 2, the tip 115 includes a nozzle at the distal end of the exit channel 215 for directing the released propellant and the compound out of the outlet orifice in a narrow plume.

Figure 3:
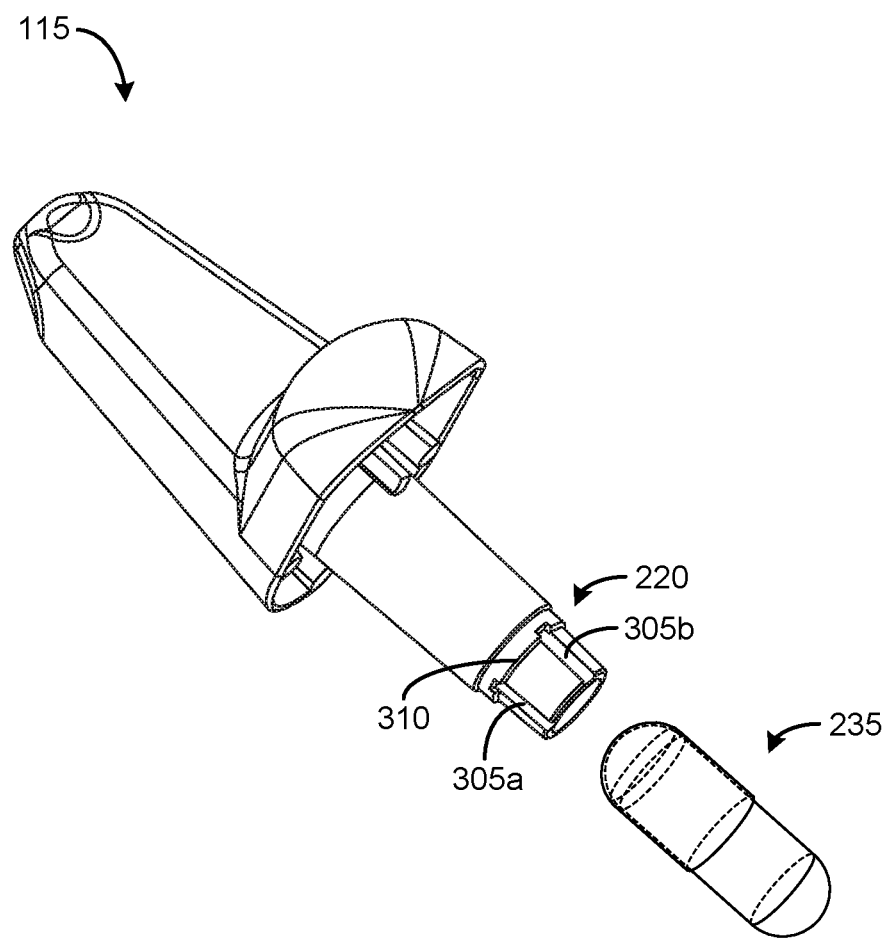
FIG. 3 is a perspective view of a tip and a capsule, in accordance with one or more embodiments.
Figure 5:
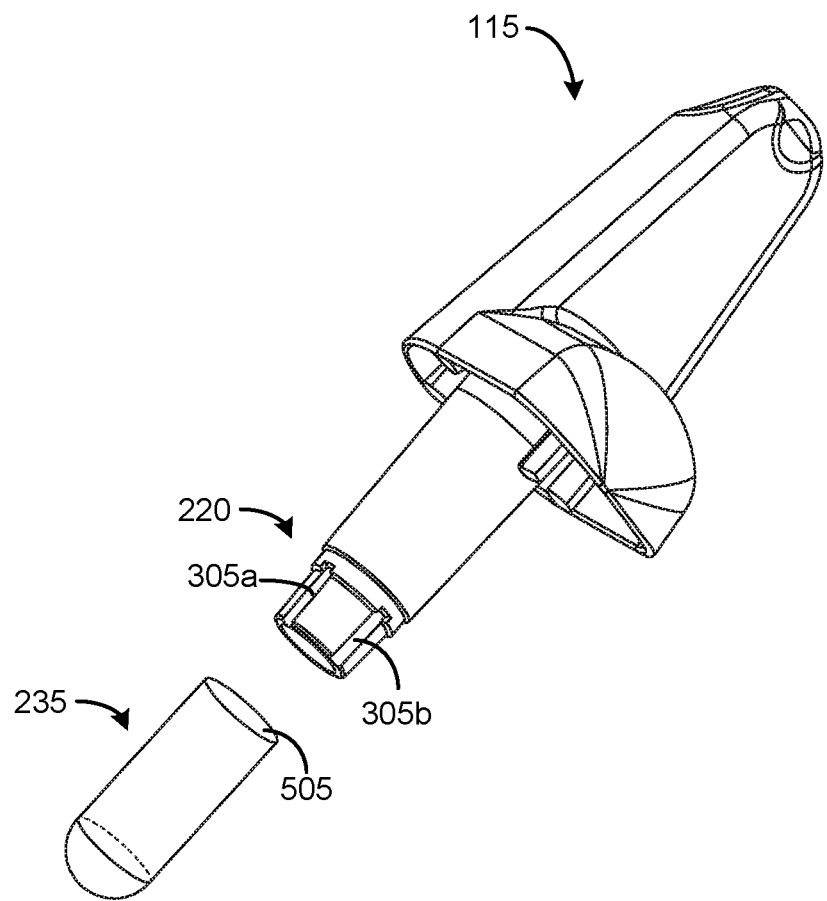
FIG. 5 is an exploded view of the tip and the capsule, in accordance with one or more embodiments.
Figure 8:
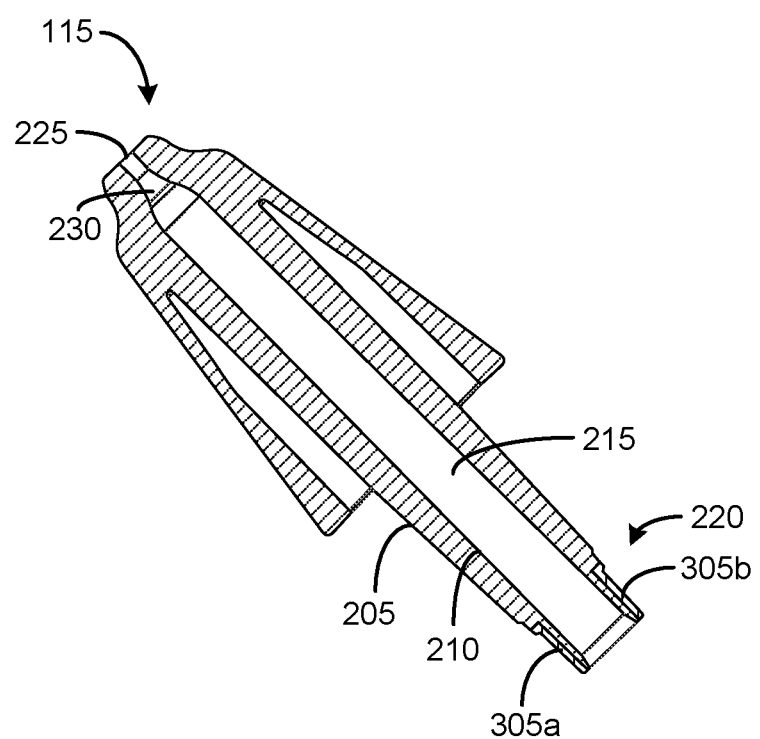
FIG. 8 is a cross-sectional view of the tip, in accordance with one or more embodiments.
Figure 9:
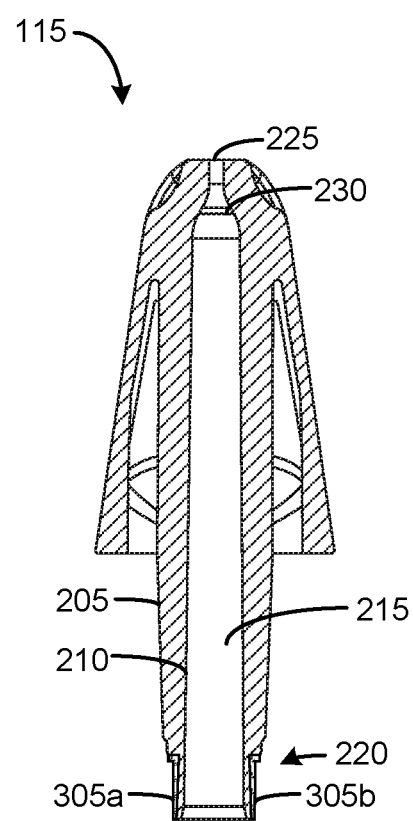
FIG. 9 is a cross-sectional view of the tip, in accordance with one or more embodiments.

FIG. 3 is a perspective view of the tip 115 and a compound container, in accordance with one or more embodiments. In the embodiment of FIG. 3, the compound container 235 is a capsule. The capsule may be comprised of two portions fitted together. When separated, a portion of the capsule (e.g., a half-capsule, as shown in FIGS. 5-7) may be coupled to the tip 115. In use, the compound container 235 may contain a compound within the capsule. In one example, the compound is a powder. As shown in FIG. 5, the half-capsule comprises an exit opening 505 of the compound container 235. The exit opening 505 may be coupled to the inlet interface 220, as shown in FIGS. 6-7. In the embodiments of FIGS. 6-7, the inlet interface 220 is inserted into the exit opening 505, and the compound container 235 may be secured to the inlet interface 220 via an interference fit. In an alternate embodiment, the exit opening 505 may be inserted into the inlet interface 220. As shown in FIGS. 7-8, the tip 115 has the outer wall 205 and the inner wall 210, where the exit channel 215 is formed by a bore or lumen through the inner wall 210. The exit opening 505 is fitted about the inlet interface 220 such that the compound container 235 and the exit channel 215 are in fluid communication.

Figure 10:
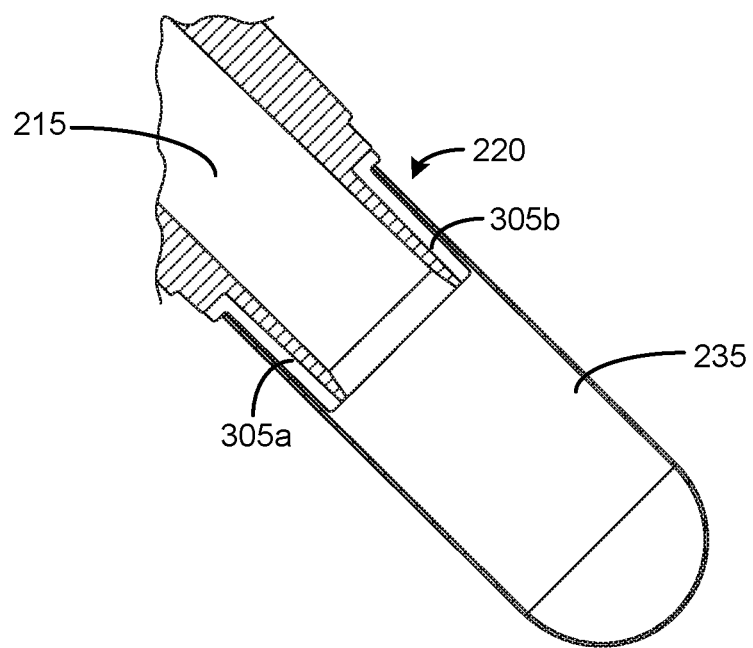
FIG. 10 is cross-sectional view of an inlet interface of the tip with the capsule attached, in accordance with one or more embodiments.

As shown in FIGS. 6, 7, and 10, the inlet interface 220 is, for example, a ring, band, port, collar, or strap interfacing with the compound container 235. As shown in FIGS. 3, 5, 6, 11A-11D, 12, and 13, one or more grooves 305 are positioned on the inlet interface 220 and create a flow path for the propellant released from the propellant canister 110 to travel into the compound container 235. An example of the grooves 305 includes but is not limited to channels, slots, radial ports, or passageways. The grooves 305 provide a pathway via the inlet interface 220 by which the propellant flows into the compound container 235. In one example, there are a plurality of grooves 305. The grooves 305 may be equally spaced about the inlet interface 220. The grooves 305 may be of equal size to each other or may be of differing sizes. The grooves 305 run along a length of the inlet interface 220 such that, when the compound container 235 is coupled to the inlet interface 220, a first portion of each groove 305 is exposed within the propellant channel 245 and a second portion of each groove 305 is positioned within the compound container 235. As shown in FIG. 3, the inlet interface 220 includes a ledge 310 that is designed to abut the compound container 235 when coupled to the inlet interface 220 and the grooves 305 extend past the ledge 310 such that the grooves 305 are not fully covered by the compound container 235.

Figure 4:
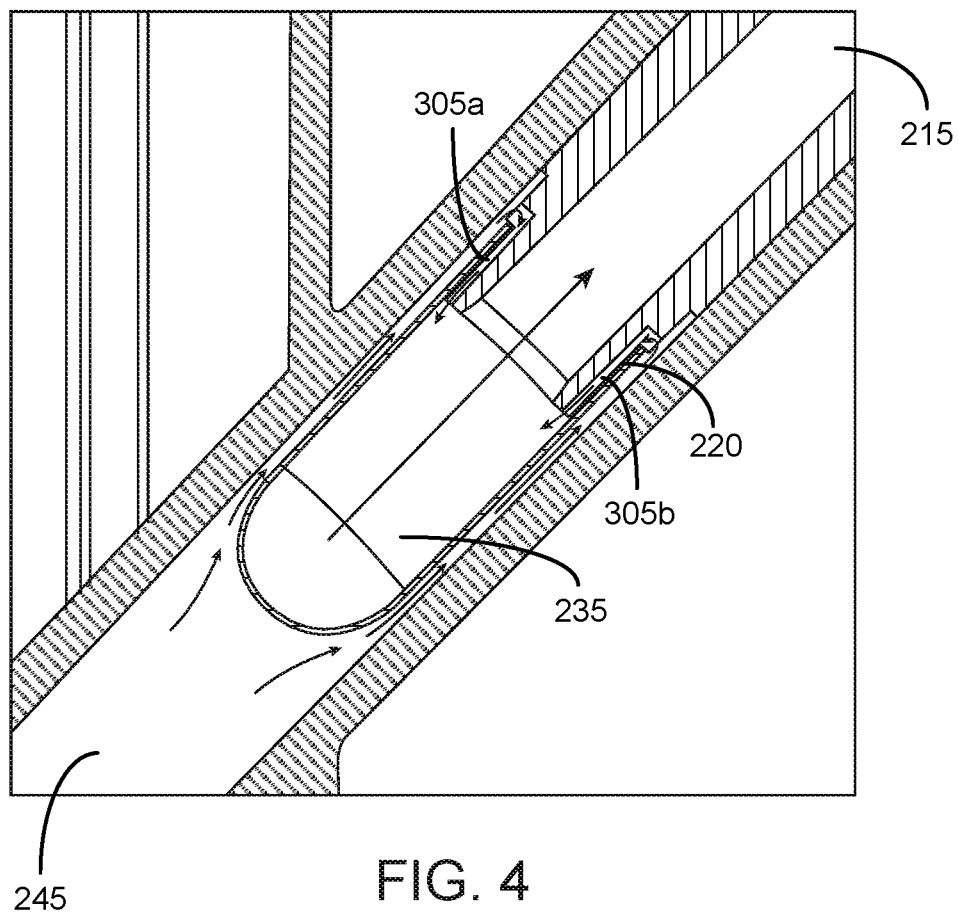
FIG. 4 is cross-sectional view of the tip and the capsule coupled to the device, in accordance with one or more embodiments.

In use, as shown by the direction of the arrows in FIG. 4, the propellant released from the canister 110 flows through the propellant channel 245 and into the compound container 235 via the grooves 305. The exit channel 215 is aligned with the exit opening 505 of the compound container 235. The propellant flows in the grooves 305 of the inlet interface 220, into the compound container 235 to agitate the powder, and the powder and the propellant exit the compound container 235 via the exit opening 505 congruent with the exit channel 215. The propellant and powder mixture are carried through the exit channel 215 through the nozzle 230 and exit the device 100 at the outlet orifice 225. In one example, the tip 115 may have one or a plurality of outlet orifices. The plume exiting the outlet orifice 225 has a narrow spray plume.

Figure 13:
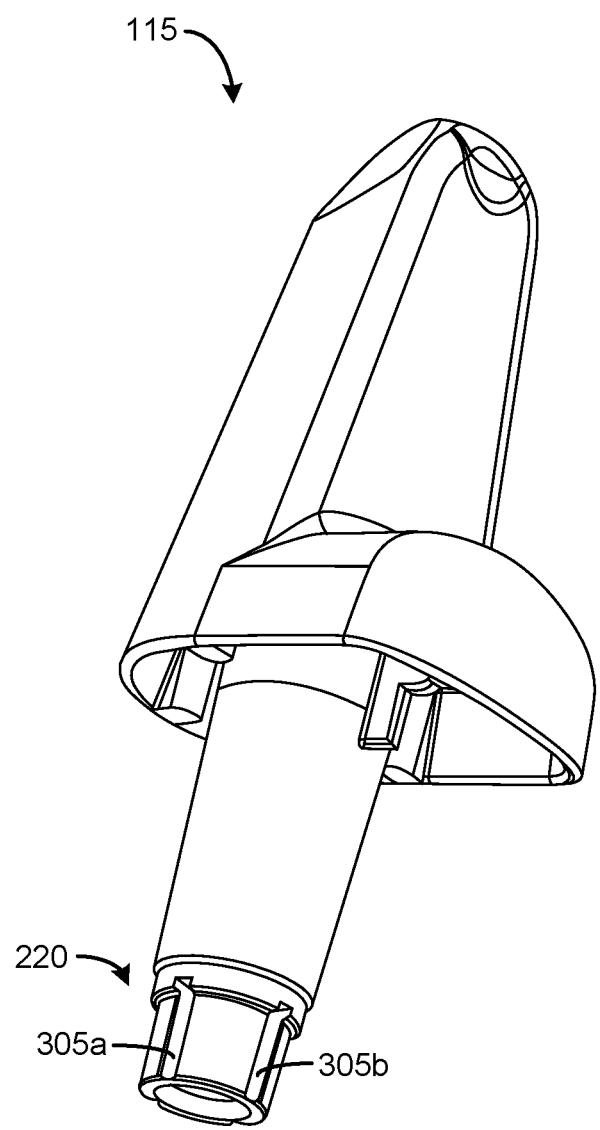
FIG. 13 is a perspective view of the tip, in accordance with one or more embodiments.
Figure 14:
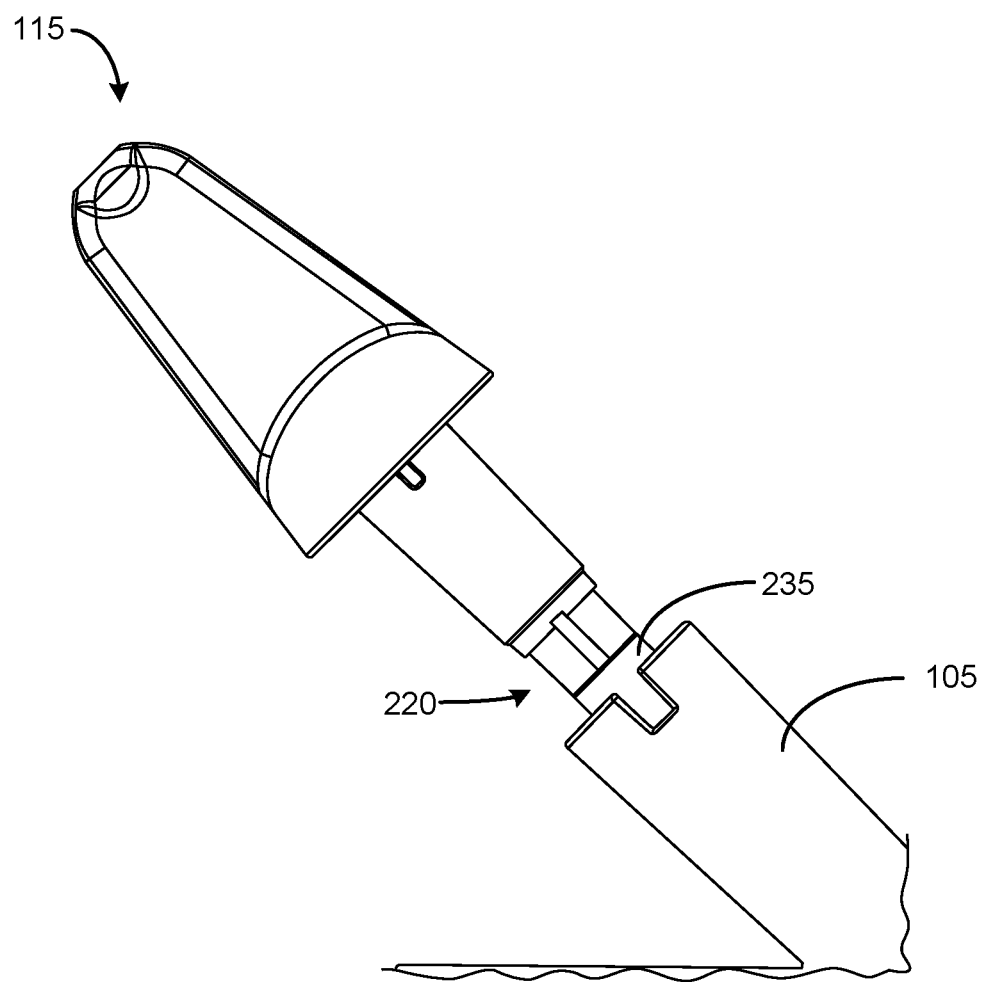
FIG. 14 is perspective view of the tip coupled to the device, in accordance with one or more embodiments.
Figure 15:
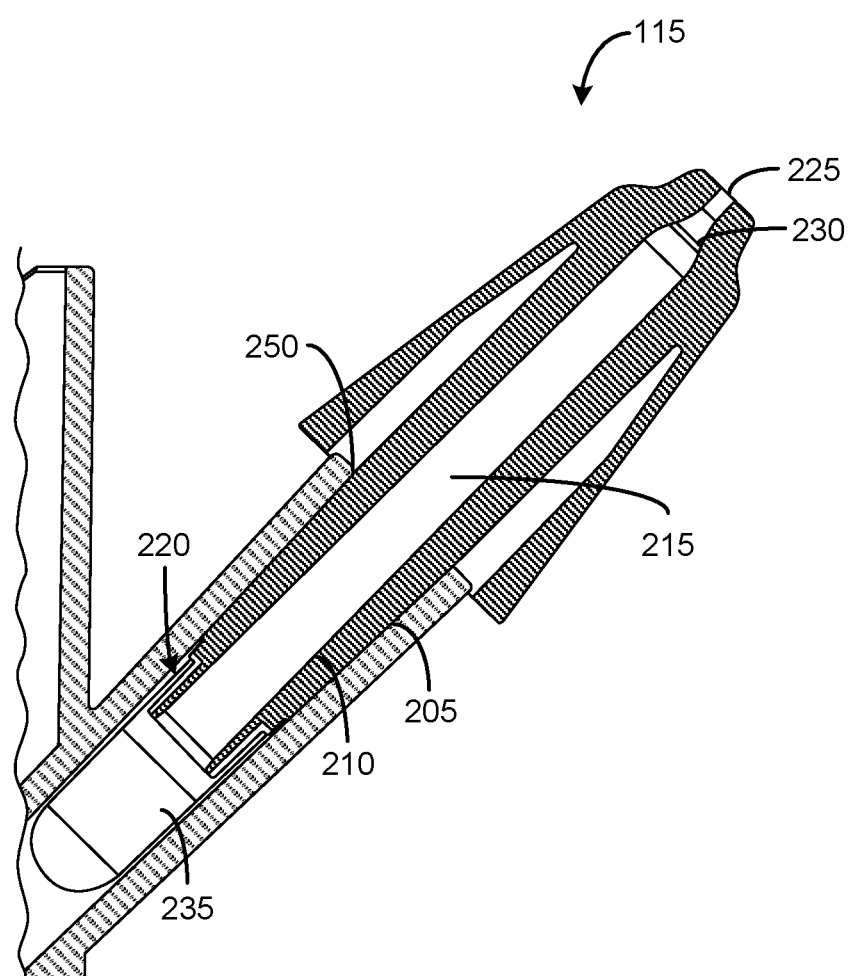
FIG. 15 is a cross-sectional view of the tip coupled to the device, in accordance with one or more embodiments.
Figure 16:
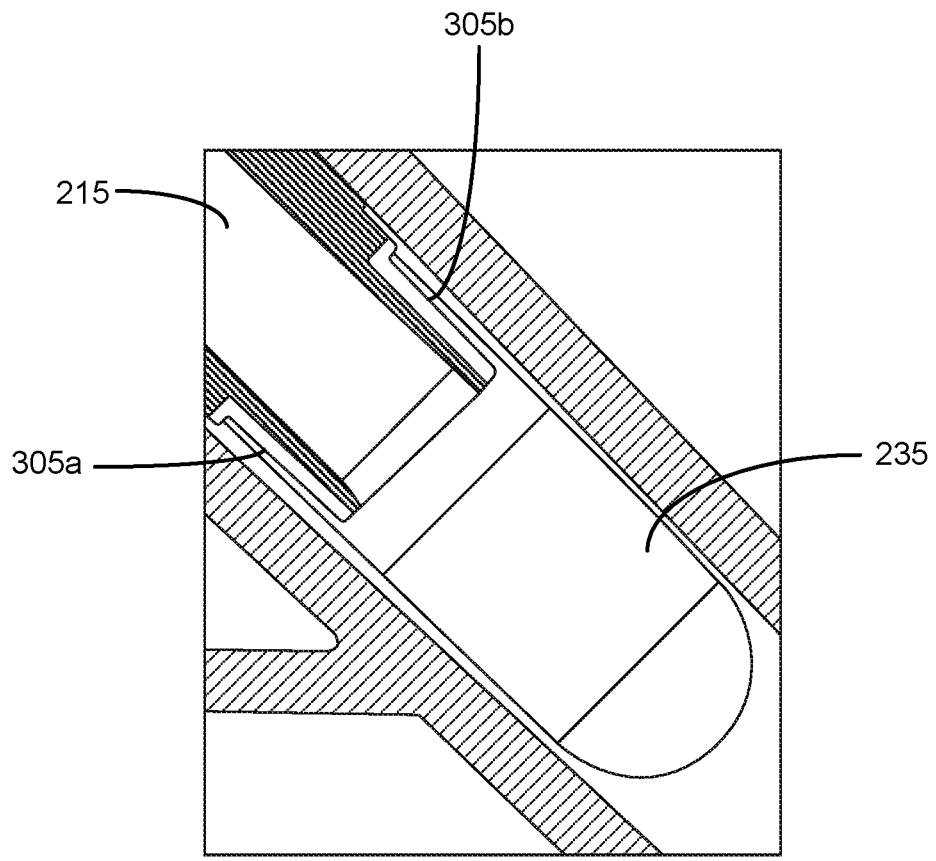
FIG. 16 is a zoomed-in view of the inlet interface with the capsule attached, in accordance with one or more embodiments.

In one example of use of the device 100, at time of use, a user separates a pre-filled capsule into its two halves. In one example, the capsule is prefilled with a powder compound. The half-capsule is coupled to the tip 115 via the inlet interface 220. As shown in FIGS. 13 and 14, the tip 115 is then coupled to the actuator body 105. A propelling gas, for example from either a refrigerant or compressed gas source, is directed through the propellant channel 245 and towards the filled powder capsule. The grooves 305 around the inlet interface 220 of the tip 115 introduce high velocity jets of propellant gas which agitate the dry powder into a suspension within the propellant gas (data not shown but confirmed with high speed close up video). Grooves 305 that introduce gas tangentially to the semispherical-shaped bottom of the compound container 235 creates jets which enhance stirring and entrainment of powder. Once the powder has been suspended, it is evacuated through the exit opening 505, into the exit channel 215, and out the outlet orifice 225 of the device 100.

Generally, when accelerating a powder formulation through a restricting orifice, any constricting junction will cause the powder to clog. Since the powder administered by this device 100 is suspended within the propellant gas prior to evacuation, it can be further throttled and directed without device clogging. As a result, a much larger mass of powder can be delivered through a much smaller outlet orifice without the device 100 being prohibitively long. The time from propellant actuation to end of compound delivery is less than 1 second.

The grooves 305 in the proximal end of the tip 115 promote gas flow into the compound container 235. In one example, the HFA gas is directed (e.g. orthogonally or near-orthogonally) at the surface of the powder dose residing in the compound container 235, which creates rapid agitation and entrainment of the powder. The semispherical shape of the compound container 235 promotes gas redirection to the exit channel 215 of the tip 115 as shown in FIG. 4. The arrows of FIGS. 2 and 4 show the direction of propellant flow after the device 100 has been actuated.

The actuator body 105 attached and seals to the propellant canister 110 and the tip 115, creating a pressurized flow path for the propellant gas. In certain aspects, the actuator body 105 is a reusable component. In certain aspects, the canister 110 is a reusable component.

In one example, the compound container 235 is a standard Size 3 drug capsule, although one of skill in the art would know how to use other sized drug capsules and modify the device 100 to fit same. Additionally, in another example, the compound container 235 may not be a capsule, but another container capable of containing a compound, such as but not limited to an ampoule. In one example, the ampoule may be made of plastic, and in one example it may be a blow fill sealed ampoule. To load the device 100, the user or clinician will separate a prefilled formulation containing capsule, discard the cap, and install the capsule over the tip 115. An empty compound container 235 can also be filled by a clinician at time of use before installing the compound container 235 onto the tip 115. In certain examples, the capsule is a disposable component.

Figure 11A:
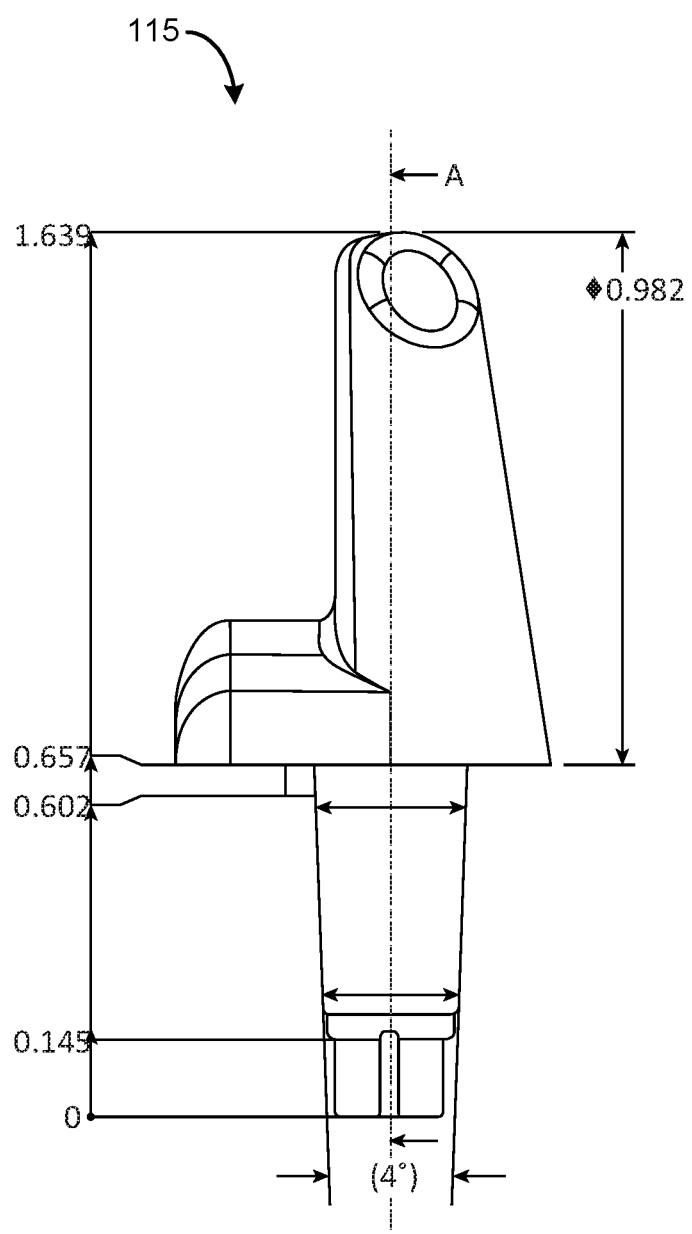
FIG. 11A-11D are cross-sectional views of a tip of the device, in accordance with one or more embodiments.
Figure 11B:
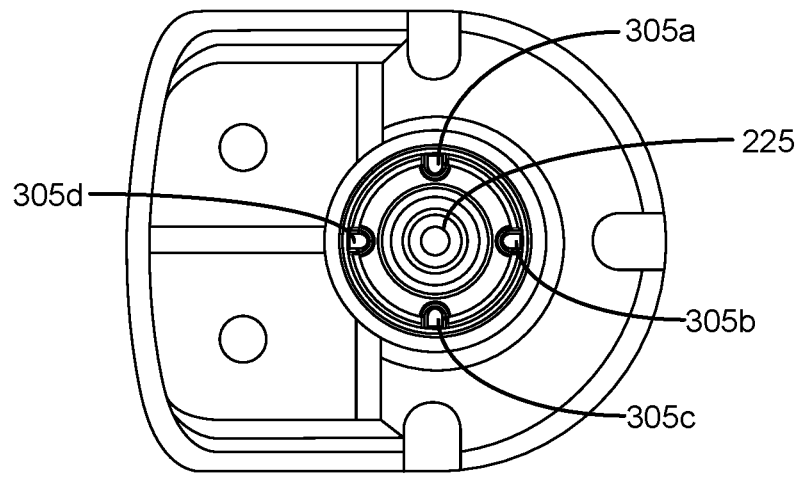
Figure 11C:
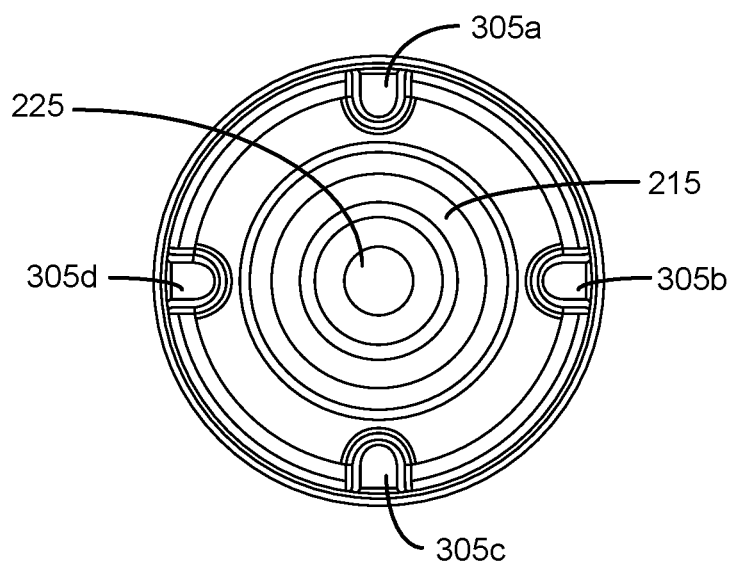
Figure 11D:
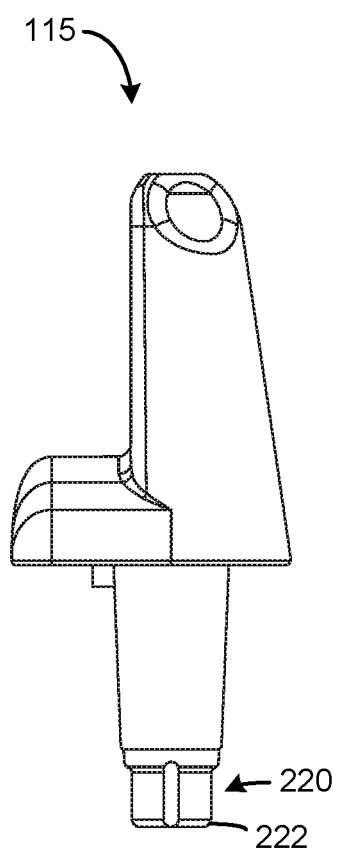
Figure 12:
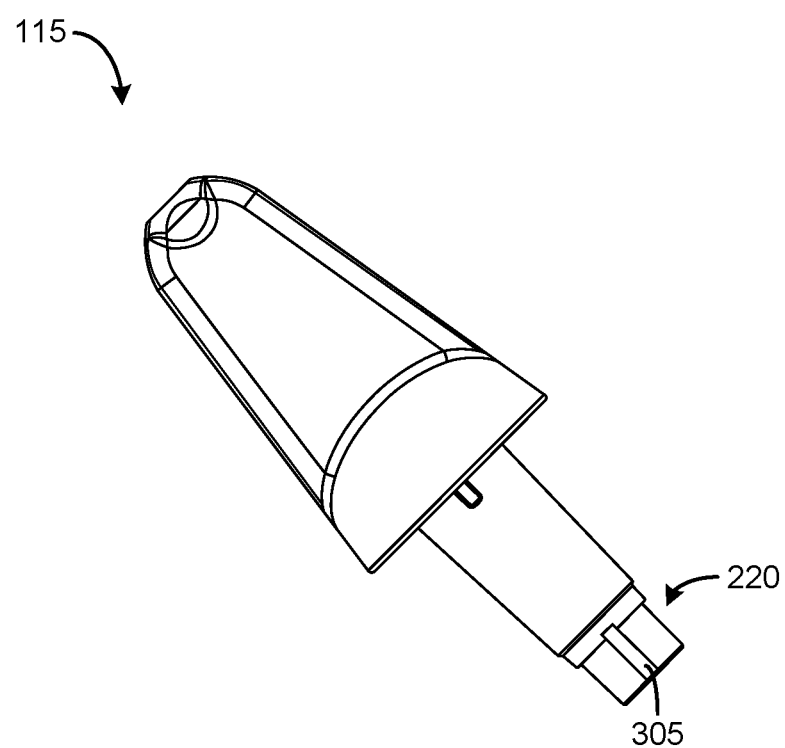
FIG. 12 is a perspective view of the tip, in accordance with one or more embodiments.

The tip 115 receives the compound container 235 during loading and is then coupled to the actuator body 105 prior to use. When the propellant canister 110 is actuated, expanding propellant gas is introduced into the compound container 235 via the grooves 305 around the inlet interface 220 of the tip 115. The resulting propellant gas jets agitate and entrain the powder formulation within the compound container 235, which then exits through the exit channel 215 and the outlet orifice 225 of the tip 115. In one example, the tip 115 is a disposable component. FIG. 11A illustrates example measurements of the tip 115 with units in inches. In the embodiment of FIG. 11D, the inlet interface 220 may include a radius along a bottom edge 222 to aid placement of the compound container 235 onto the tip 115. The radius of curvature may range between approximately 0.005 inches to 0.025 inches, inclusive.

Figure 17:
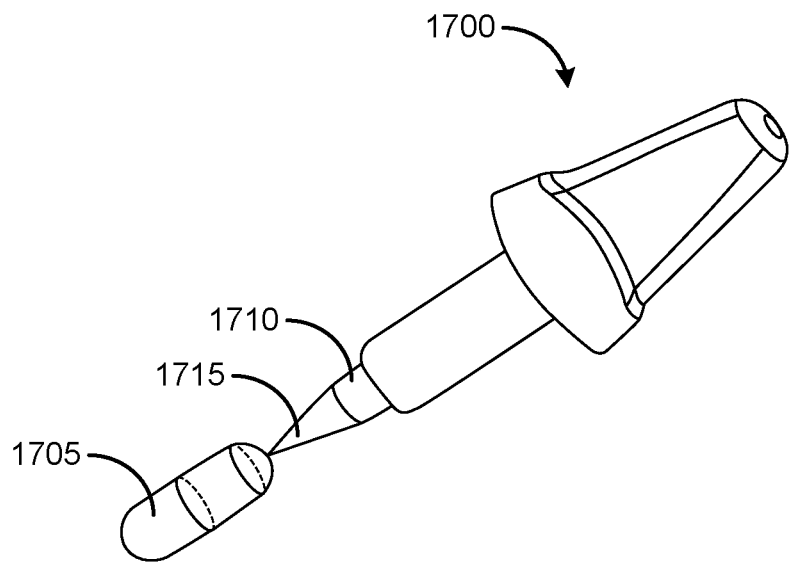
FIG. 17 is a perspective view of a second embodiment of a tip, in accordance with one or more embodiments.
Figure 18:
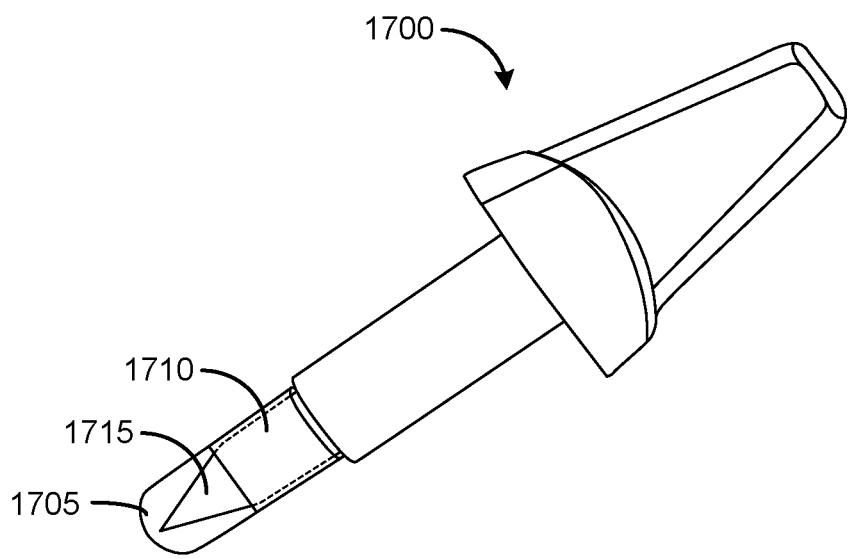
FIG. 18 is a perspective view of the tip of FIG. 17 with a capsule attached, in accordance with one or more embodiments.
Figure 19:
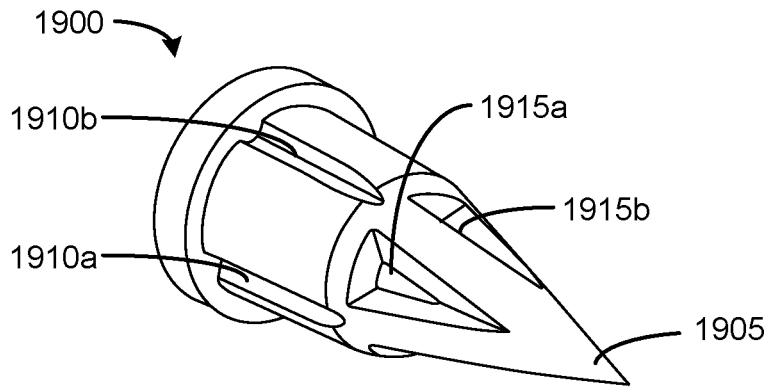
FIG. 19 is a perspective view of a puncture member, in accordance with one or more embodiments.
Figure 20:
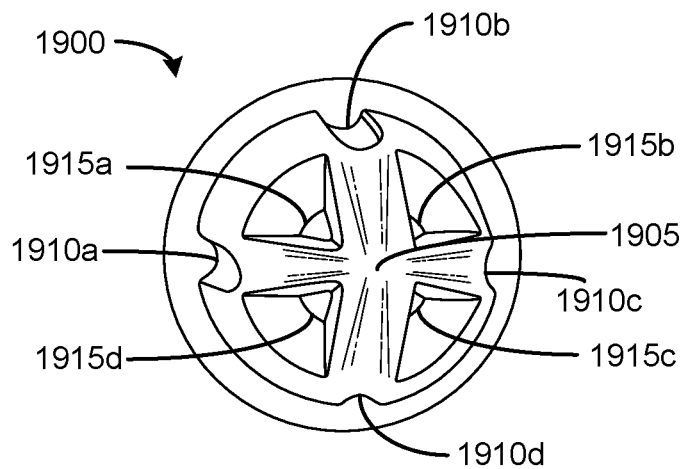
FIG. 20 is a perspective view of the puncture member, in accordance with one or more embodiments.
Figure 21:
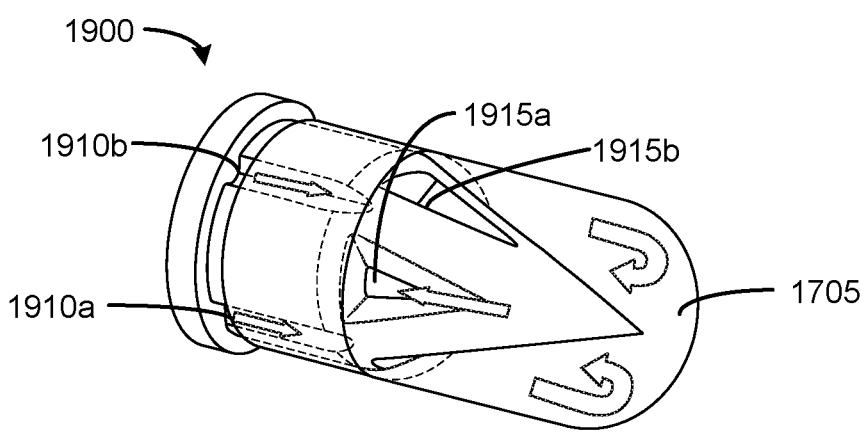
FIG. 21 illustrates a flow path of the second embodiment of the device, in accordance with one or more embodiments.

FIGS. 17-18 illustrate perspective views of a second embodiment of a tip 1700. Similar to the tip 115, the tip 1700 may be coupled and decoupled to the actuator body 105, which enables a user to load and unload a compound container 1705 to and from the tip 1700 for delivery to an upper nasal cavity of a user using the device 100. As shown in FIGS. 17-18, a compound container 1705 is a capsule. The compound container 1705 may, in one example, contain a powder. In the embodiments of FIGS. 17-18, the tip 1700 includes an inlet interface 1710 for coupling the compound container 1705, where the inlet interface 1710 has a puncture member 1715. The puncture member 1715 is designed to puncture the compound container 1705 to create an opening in the compound container 1705. The puncture member 1715 may comprise a sharp point, a sharp angle, a blade-like edge, or other suitable geometries for puncturing the compound container 1705. In one embodiment, the inlet interface 1710 includes more than one puncture member 1715, where each puncture member 1715 is designed to puncture the compound container 1705. The puncture members 1715 may be positioned about the inlet interface 1710 in a pattern, symmetrically, or at random. In one example, in use, a user may remove the tip 1700 from the actuator body 105, load the compound container 1705 into the port 250 of the propellant channel 245, and then insert the tip 1700 back into the port 250. As the tip 1700 is coupled to the actuator body 105, the puncture member 1715 punctures the capsule. In this configuration, the punctured capsule fits around the puncture member 1715, as shown in FIG. 18. In alternate embodiments, the puncture member 1900 may comprise a plurality of puncture points 1905 that each puncture the compound container 1705. The plurality of puncture points 1905 may be spaced about the puncture member 1900, or each FIGS. 19-20 illustrate perspective views of a puncture member 1900 that may be used with the tip 1700, in accordance with one or more embodiments. As shown in FIG. 19, the puncture member 1900 may be a collar, ring, band, port or strap that couples with the punctured compound container 1705. The puncture member 1900 includes one or more puncture grooves 1910 that, similar to grooves 305, form a flow path between the propellant channel 245 and the compound container 1705. The propellant from the propellant canister 110 enters via the one or more puncture grooves 1910 of puncture member 1900 and flows along the puncture grooves 1910 and into the punctured compound container 1705. As shown in FIGS. 19-20, the puncture member 1900 includes a plurality of puncture openings 1915. In the embodiments of FIGS. 19-21, the puncture openings 1915 are in fluid communication with the exit channel 215. The propellant from the propellant canister 110 flows into the puncture grooves 1910, mixes with the powder in the punctured compound container 1705, and flows into the puncture openings 1905 to the exit channel 215. The arrows of FIG. 21 illustrate the flow path of the propellant. The exit channel 215 provides a route for the propellant and the powder to the nozzle 230 and the outlet orifice 225. The mixture of propellant and powder exit the device 100 via the outlet orifice 225. The plume exiting the device 100 is a narrow spray plume. In this embodiment, the puncture member 1900 may be integrally molded as a single piece or may consist of two or more pieces. In one example, the puncture member 1900 may be a separately molded piece acting in association with the inlet interface 1710 (where the capsule attaches). In some embodiments, an inlet interface may include more than one puncture member 1900.

As shown in FIGS. 19 and 20, as an alternate to the capsule being manually separated prior to placement on the tip 1700, the tip 1700 may include an integrated puncture member 1900 and puncture grooves 1910. In order to create a repeatable puncture of the compound container 1705, a puncture member 1900 comes to a single point, puncture point 1905. In one example, the puncture point 1905 includes puncture openings 1910 that are radially spaced about the puncture point 1905. The puncture openings 1910 are in fluid communication with the exit channel 215 for the powder to be evacuated from the compound container 1705.

As shown in FIG. 21, by allowing the propellant flow path to be created with an inline puncture motion, loading the compound container 1705 onto the tip 1700 is simplified for the user, as the compound container 1705 does not require manual manipulation and separation. In one example, the puncture member 1900 is formed integrally with the tip 1700. In one example, the filled compound container 1705 may be filled and installed into either the actuator body 105 or the tip 1700 during manufacturing of the device 100. At time of use, a user may apply a linear motion to drive the puncture member 1900 into the pre-filled compound container 1705, creating a complete gas flow path for dosing prior to propellant actuation.

The invention is further described in the following examples, which are not intended to limit the scope of the invention.

Example 1

Powder Capsule

In one embodiment, a device was constructed and tested. Testing was conducted for residual powder in the compound container after actuation. The device has equivalent performance of powder delivery, as determined by residuals after actuation, when 2 or more but less than 6 grooves on the inlet interface are used. In this example, the grooves are in combination with 63 mg of HFA propellant and a 0.040" outlet orifice of the nozzle. Four grooves (every 90 degrees) were found to provide uniform gas delivery.

Dose Mass

Dose mass reproducibility testing was conducted. The standard deviation on dose delivery shows the device is capable of delivering consistent dose masses. The mean residual of dose left in the device was <5%, showing very little dose is lost in the device.

TABLE 1

Mass reproducibility of final molded device, Values in milligrams

| | |
|---|---|
| n | 49 |
| Mean (mg) | 34.9 |
| Standard Deviation | 1.0 |
| Min | 32 |
| Max | 36.7 |
| Range | 4.7 |
| Mean % Residual | 3.8% |

Additional Configuration Information

The foregoing description of the embodiments of the disclosure has been presented to for the purpose of illustration; it is not intended to be exhaustive or to limit the disclosure to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed:

1. A device for delivering a compound to an upper nasal cavity comprising:
    an actuator body comprising:
        a propellant channel configured to be in fluid communication with a canister containing a propellant; and
    a tip configured to removably couple to the actuator body, the tip comprising:
        an outer wall and an inner wall, the inner wall forming an exit channel that extends between a proximal end and a distal end of the tip;
        an inlet interface positioned about a distal end of the outer wall, the inlet interface configured to couple to a compound container containing the compound;
        one or more grooves positioned about the inlet interface, such that, when the compound container is coupled to the inlet interface, a first portion of each groove is exposed within the propellant channel and a second portion of each groove is positioned within the compound container and wherein each groove is in fluid communication with the propellant channel and the exit channel; and
        an outlet orifice disposed at a distal end of the exit channel, such that propellant released from the canister travels through the propellant channel and into the compound container via the one or more grooves, thereby contacting the compound and propelling the compound through the exit channel and out the outlet orifice.

2. The device of claim 1, wherein the compound is a liquid or a powder.

3. The device of claim 1, wherein the compound container is a capsule.

4. The device of claim 1, wherein the inlet interface is a collar positioned at the proximal end of the tip, wherein the collar is configured to be inserted into the compound container.

5. The device of claim 1, wherein the inlet interface comprises a puncture member that is configured to puncture the compound container.

6. The device of claim 5, wherein the puncture member comprises one or more openings that are in fluid communication with the exit channel.

7. The device of claim 6, wherein the one or more openings are positioned radially symmetric about the puncture member.

8. The device of claim 5, wherein an inline force provided to the tip by a user is configured to translate the tip relative to the actuator body such that the puncture member punctures the compound container.

9. The device of claim 1, wherein the tip is configured to be removably coupled from the actuator body for coupling the compound container to the inlet interface.

10. The device of claim 1, further comprising a nozzle congruent with the exit channel.

11. The device of claim 1, wherein the compound container is configured to couple to the inlet interface with an interference fit.

12. The device of claim 1, wherein the one or more grooves are configured to direct propellant released from the canister into the compound container in an orthogonal direction relative to a bottom surface of the compound container.

13. The device of claim 1, further comprising the compound container, wherein the compound container is prefilled with the compound.

* * * * *